United States Patent [19]
Hinton et al.

[11] Patent Number: 6,033,630
[45] Date of Patent: Mar. 7, 2000

[54] METHOD AND SENSOR FOR DETECTING VOLATILE ENANTIOMERIC SUBSTANCES IN GASES

[76] Inventors: Andrew John Hinton, 20 The Verne, Church Cookhan, Fleet, Hampshire; Michael Cooke, Royal Holloway University of London, Egham Hill, Egham, Surrey, both of United Kingdom

[21] Appl. No.: 08/812,090

[22] Filed: Mar. 4, 1997

[30] Foreign Application Priority Data

Mar. 4, 1996 [GB] United Kingdom ............ 9604627

[51] Int. Cl.⁷ .................................................. G01N 27/04
[52] U.S. Cl. ...................... 422/98; 422/88; 436/149; 436/153; 73/23.34; 73/31.01; 73/31.02; 73/31.05; 73/31.06; 338/13; 338/34
[58] Field of Search .............. 422/88, 98; 436/149, 436/153; 73/23.34, 31.01, 31.02, 31.05, 31.06; 338/13, 34

[56] References Cited

U.S. PATENT DOCUMENTS 5,244,562 9/1993 Russell .................................. 204/418

*Primary Examiner*—Jill Warden
*Assistant Examiner*—Sharidan Carrillo
*Attorney, Agent, or Firm*—Finnegan, Henderson, Farabow, Garrett & Dunner, L.L.P.

[57] ABSTRACT

A method and sensor for distinguishing between different optical isomers (enantiomers), which sensor comprises a pair of spaced-apart contacts and a semi-conductive polymer material spanning the gap between the contacts, which polymer material includes chiral sites. The chiral sites in the polymer material are preferably formed by incorporating an optically active counterion into the polymer material, for example by growing the polymer in the presence of such a counterion, e.g. camphor sulphonic acid.

13 Claims, 7 Drawing Sheets

R=1.00%

CURSOR AT 01:00

METHOD AND SENSOR FOR DETECTING VOLATILE ENANTIOMERIC SUBSTANCES IN GASES

TECHNICAL FIELD

The present invention relates to the sensing of gases, volatile materials and in particular to the sensing of smells, aromas or odours.

Background Art

It is known that the smell of certain naturally occurring volatile materials, as perceived by the human nose, is dependent upon the optical activity of the volatile material. For example, d-carvone smells of caraway and dill while the corresponding l-carvone smells of spearmint. It is thus highly desirable to be able to distinguish between different optical isomers (enantiomers). However, optical isomers have identical physical properties to each other and it is therefore difficult to tell the isomers apart using simple analytical techniques without separating out the individual isomers and no such simple technique has hitherto been able to achieve this.

Although optically active aroma materials can be produced synthetically. synthetic production generally produces a racemic mixture of the isomers and the separation of the racemic mixture into its constituent isomers is very expensive. The aroma effect of the racemic mixture is often different from that of the naturally occurring isomer. On the other hand, synthetically produced racemic aroma materials are much cheaper than their naturally occurring counterparts.

It is possible, in order to save costs, to incorporate a limited amount of the synthetic material in with the naturally-occurring material without a significantly noticeable effect on the overall aroma but there is a limit to how much synthetic material can be incorporated before it does have a noticeable effect. For example, l-menthol is added to toothpaste to give it a peppermint flavour. l-menthol is naturally occurring but it can also be produced synthetically in a racemic mixture. The racemic mixture of d- and l-isomers is much cheaper than the naturally occurring l-menthol but, as stated, there is a limit on how much synthetic menthol can be added before the user notices. It is therefore highly desirable to be able to detect the difference between synthetic and naturally occurring menthol to control the amounts of the natural and synthetic menthol added to toothpaste.

The present invention provides a simple sensor that is capable of producing a signal that distinguishes between different enantiomers.

It is known from GB-2176901, GB-2221761, WO93/03355 and WO86/01599 to make sensors for sensing the presence of volatile materials, e.g. smells, aromas and odours, in a gaseous atmosphere. Such sensors consist of a pair of spaced-apart electrical contacts and a semi-conductive polymer spanning the gap between the contacts. The resistance of the polymer changes on exposure to a volatile material, the magnitude of the resistance change depending firstly on the nature and amount of the volatile material and secondly on the nature of the polymer.

It is also known to provide a sensing head for analysing a volatile material that comprises an array of such sensors, each containing a different polymer. The different polymers in the sensors of the head respond differently to the presence of a volatile material, e.g. an aroma, in the atmosphere being monitored. The resistance of the polymers of the various sensors sensor head are monitored to give an output signal for each sensor, which may, in effect, be a plot of the resistance of the polymer of each sensor against time. The combination of signals from the various sensors gives a pattern that is characteristic of the aroma concerned and the pattern of sensor signals for a given aroma is often referred to as a "fingerprint" of that aroma. The combination of sensor signals obtained on exposure of the sensor head to a volatile material can be used to detect, characterise and identify the smell, aroma or odour.

The sensors are made by laying down on a substrate a pair of spaced-apart contacts and the polymer is grown (polymerised) electrolytically in the gap between the contacts by dipping the spaced-apart contacts into a monomer solution that also contains a counter ion and a solvent. When an electric current is passed between, on the one hand, the contacts and, on the other hand, a counter electrode, the monomer is polymerised in the gap between the contacts. The properties of the polymer within the sensor is determined, not only by the monomer, but also by the counterion present in the monomer solution, which is incorporated into the polymer to balance the ionic charge of the polymer chain. Also the properties of the polymer are affected by the nature of the solvent in the original monomer solution.

DISCLOSURE OF THE INVENTION

According to the present invention, there is provided a sensor capable of distinguishing between different enantiomers, which sensor comprises a pair of spaced-apart contacts and a semi-conductive polymer material spanning the gap between the contacts, which polymer material includes chiral sites.

The chiral sites in the polymer material may be formed by:

1. including optically active groups in the polymer, generally in a side group bonded to the chain, for example, when the polymer is polypyrrole, the chiral side chains may be bonded to one of the carbon atoms or to the nitrogen atom of the pyrrole ring in the oxidised polypyrrole;
2. incorporating an optically active counterion into the polymer material, for example by growing the polymer in the presence of such a counterion; examples of such counterions are menthoxy acetic acid, carzyl acetate and natural or synthetic chiral amino acids such as cysteine and valine, or
3. growing the polymer from a monomer solution whose solvent is optically active.

Although sensors as described in WO 93/03355 are capable of detecting aromas and the human nose is also capable of detecting aromas, the sensors themselves do not actually mimic the action of the nose since the sensors and the nose use completely different mechanisms for detecting aromas, the sensors detecting the conductivity of the polymer in the presence of the aromas while the human nose detects aromas because the aroma triggers nerve cells In the nose that the brain responds to. It is thus totally unexpected and surprising that the sensors can detect differences in enantiomers in this way, particularly since the physical properties of the enantiomers are identical to each other (apart from their effect on polarised light).

The polymer may be a copolymer.

Of the above three possibilities of including a chiral site, possibility 2 is preferred since it is easier to incorporate chiral counterions into the polymer material during the growth of the polymer chain than to incorporate such sites into the polymer itself, since steric effects can lead to problems in polymerising monomers having chiral sites. The use of optically active solvents in the monomer solution can give the desired discrimination between enantiomers, but it is less reliable than the use of optically active counterions and/or optically active sites in the polymer itself.

The optically active anionic counterion preferably includes a sulphonic acid (sulphonate) group since that stabilises the polymer material in air. The sulphonic acid group is preferably bonded directly to the optically active site although this is not an absolute necessity.

The counterion is preferably a compound of a general formula:

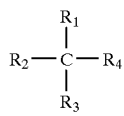

wherein $R_1$, $R_2$, $R_3$ and $R_4$ are all different and stand for different organic or inorganic substituents; preferably at least one of the substituents is or contains one or more sulphonate group(s) (although it is apparent that two or more of the substituents $R_1$ to $R_4$ cannot stand for sulphonate alone). Most preferred are commercially available optically active compounds, especially camphor sulphonic acid, which gives rise to the camphor sulphonate anion.

When the optically active site is included in the polymer chain, it is generally included in a side chain to the polymer backbone, for the reasons given above. Any natural or synthetic optically active side group may be used so long as it can be introduced into the polymer chain. Example of such side groups are radicals formed from menthoxy acetic acid, carzyl acetate and natural or synthetic chiral amino acids such as cysteine and valine.

The chiral sites may be introduced into the polymer by an optically active solvent. In these circumstances, any suitable optically active solvent may be used.

The present invention also contemplates a method of detecting and discriminating between different chiral compounds, which comprises exposing a sensor of the type described above to a gaseous sample containing an optically active substance and measuring the resistance of the polymer material.

The present invention is not limited to the detection of aroma materials and can be used to detect gases and volatile materials that are odourless to the human nose. The gaseous sample may be the gas or vapour in the headspace above a volatile liquid or solid.

BEST MODE FOR CARRYING OUT THE INVENTION

Example 1

Figure 7:
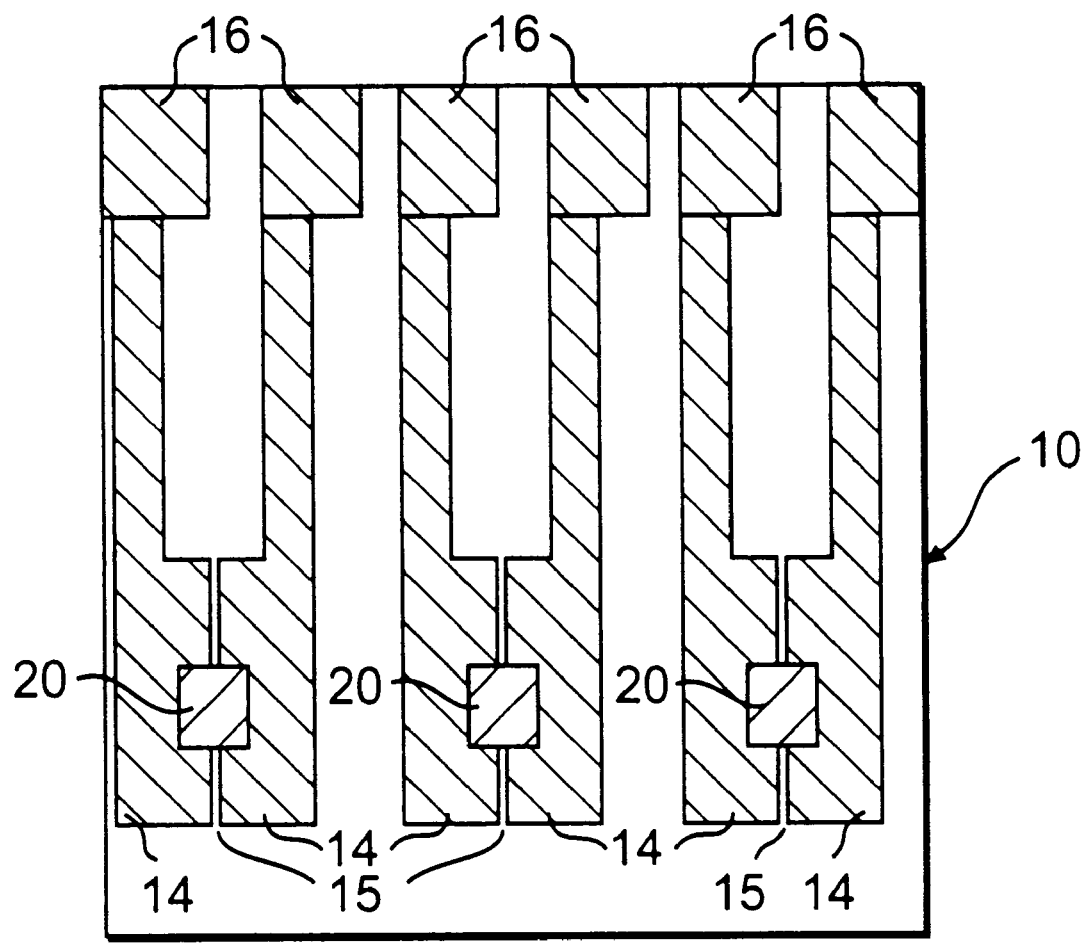
FIG. 7 is a schematic view of three sensors of the present invention mounted on a common base.

A substrate containing three sensors of the present invention is made in the manner disclosed in WO93/03355 (the content of which is incorporated herein by reference). The substrate (see FIG. 7) includes a base 10 of silicon, alumina or silica on which there are deposited three pairs of contacts 14 (one pair for each sensor). the contacts of each pair being spaced apart by a gap 15 of approximately 10 μm. Electrical connections to the individual contacts 14 can be made by conductive pads 16. The whole of the substrate (except in the area of the pads 16 and in the area of a window 20 overlying both the gap 15 and adjacent areas of the contacts) is covered by a layer of an insulating stop-off material (not shown for ease of illustration). Details for the manufacture of the substrate are disclosed in WO93/03355.

25 ml of 0.1M (1R)(−)-10-camphor sulphonic acid solution (the solvent being deionised water) is measured into a beaker and 0.25 grams of purified pyrrole are added drop by drop using a teat pipette. The resulting pyrrole solution is stirred with a glass rod.

The substrate is immersed in the pyrrole solution so as to cover the window 20 where the polypyrrole will be grown. A saturated calomel reference electrode and a platinum gauze secondary (counter) electrode are also inserted into the solution. The contacts 14 of the substrate and the secondary and the reference electrodes are then all connected to a conventional potentiostatic circuit that maintains a potential of +850 millivolts between, on the one hand, the contacts 14 and, on the other hand, the reference electrode. This causes the pyrrole to polymerise in the window 20 of each sensor. After two minutes, the potentiostatic circuit is switched off and the polypyrrole grown on the substrate is allowed to equilibrate with the pyrrole solution for a further two minutes before being removed from the solution and rinsed with distilled water. The substrate is allowed to dry for 24 hours.

Example 2

The procedure described in Example 1 is followed except that the (1S)(+) enantiomer of camphor sulphonic acid is used instead of the (1R)(−) enantiomer.

Example 3

Figure 1:
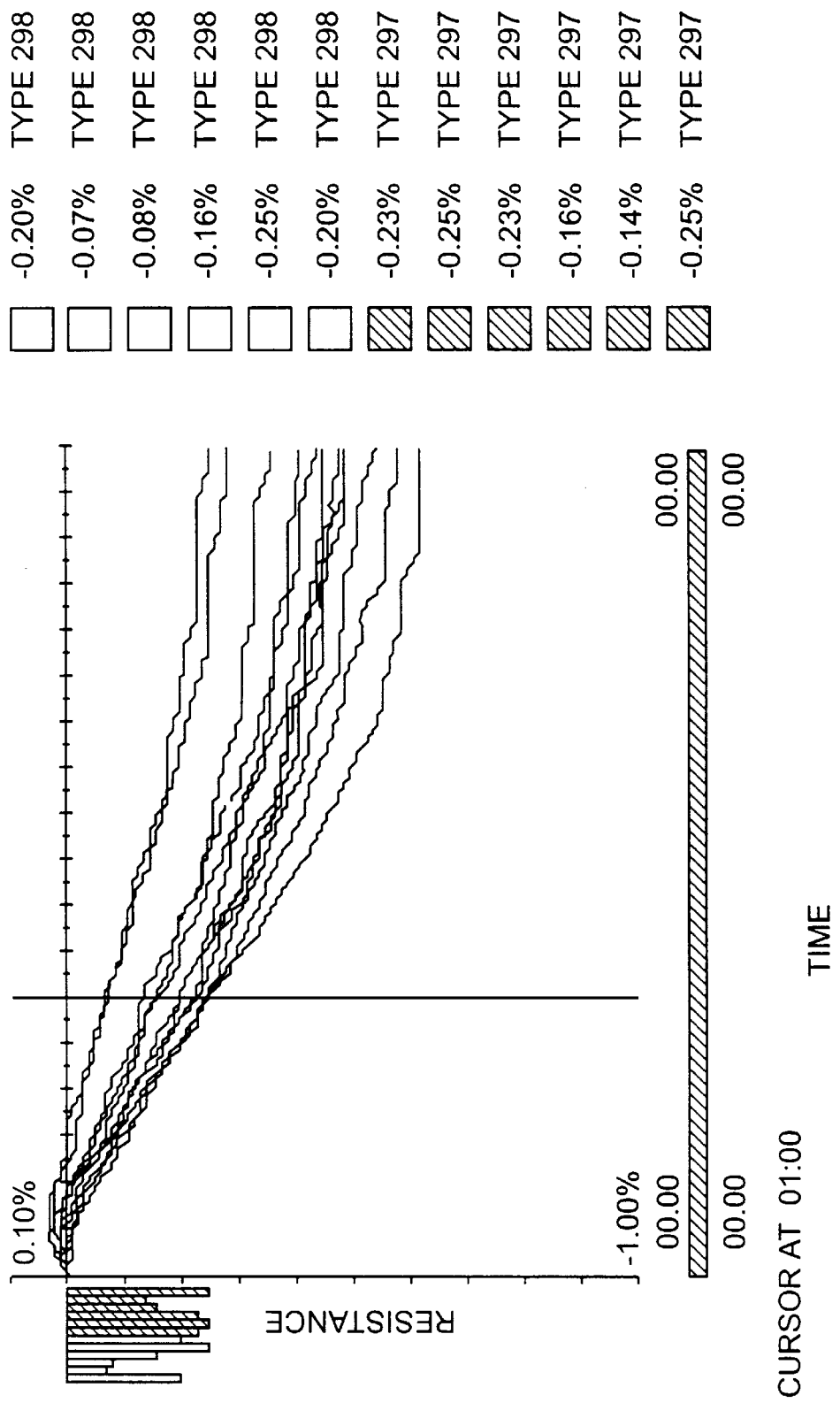
FIG. 1 is a graph showing the signals (against time) from twelve sensors according to the present invention on exposure of the sensor to (S)-(+)-2-amino-1-butanol.

Six sensors of the type described in Example 1 and six sensors of the type described in Example 2 are mounted on a sensor head of a type commercially available from Neotronics Scientific Limited of Western House, 2 Cambridge Road, Stansted Mountfitchet, Essex, United Kingdom and each is connected to a circuit for measuring the resistance of the polypyrrole deposited in the window 20. This involves applying a potential difference between the contacts 14 of each sensor so that an electrical current passes through the polypyrrole; the magnitude of the current flowing will give a measure of the resistance of the polymer. These sensors are then exposed to an atmosphere containing (S)-(+)-2-amino-1-butanol at a temperature of approximately 20° C. and the resulting signals from the various sensors are shown in FIG. 1 where the vertical axis is the sensor signal (i.e. change in resistance) and the horizontal axis denotes time in minutes. The sensors are then removed from the 2-amino-1-butanol atmosphere and allowed to equilibrate in dry air for a period of at least 5 minutes.

Figure 2:
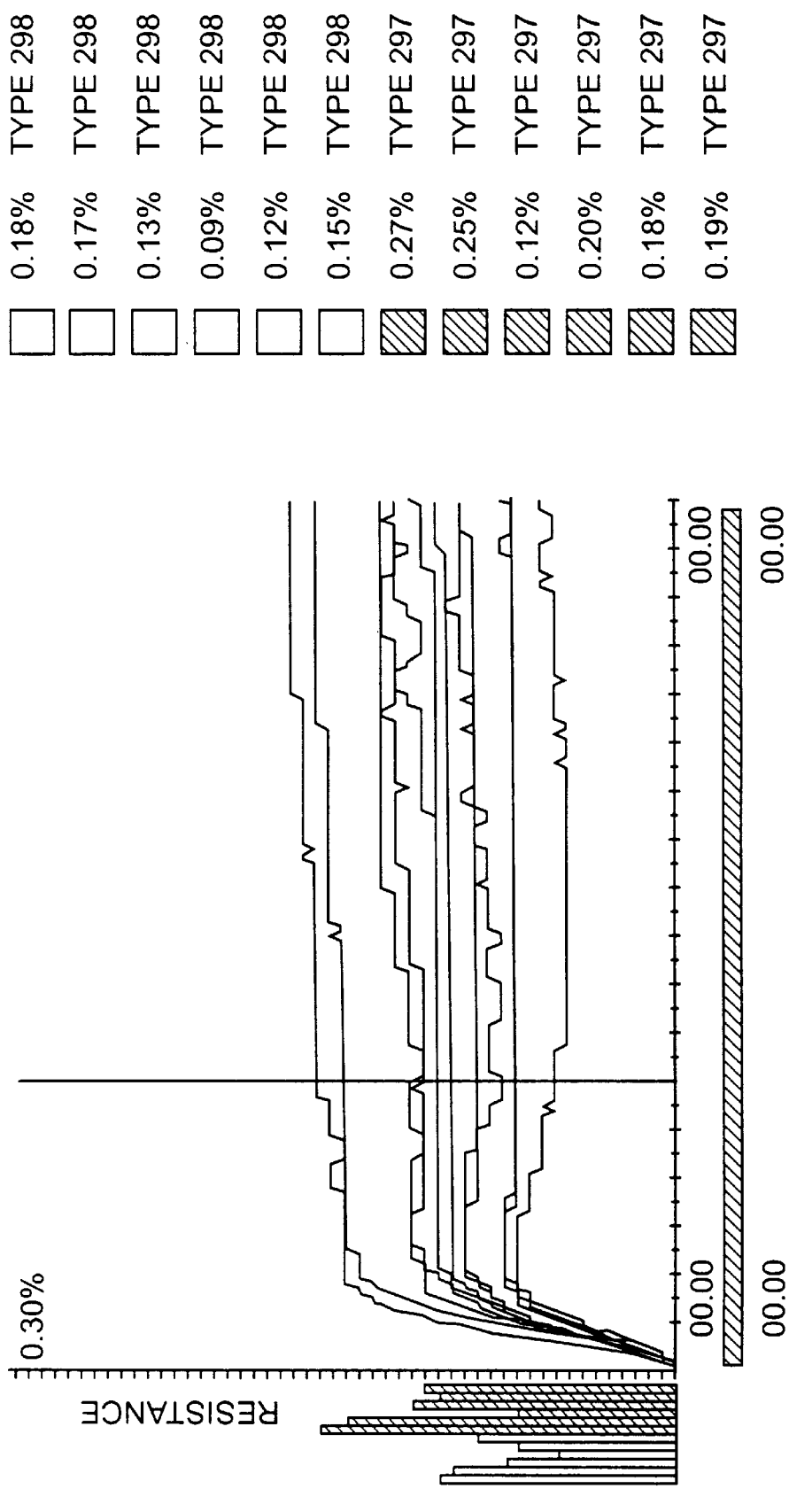
FIG. 2 is a graph corresponding to FIG. 1 when the same twelve sensors are exposed to (R)-(−)-2-amino-1-butanol.

The sensors are then exposed to an atmosphere containing the (R)-(−) enantiomer of 2-amino-1-butanol and the resulting signals from the sensors are shown in FIG. 2.

It is apparent from the graph of FIGS. 1 and 2 that the two types of sensors are able to discriminate between the two enantiomers of 2-amino-1-butanol and also that the signals from the sensors of Example 1 give qualitatively similar signals to the two chiral gas samples as the sensors of Example 2, despite the polymers in the two sensors having opposite chiral sites.

Figure 3:
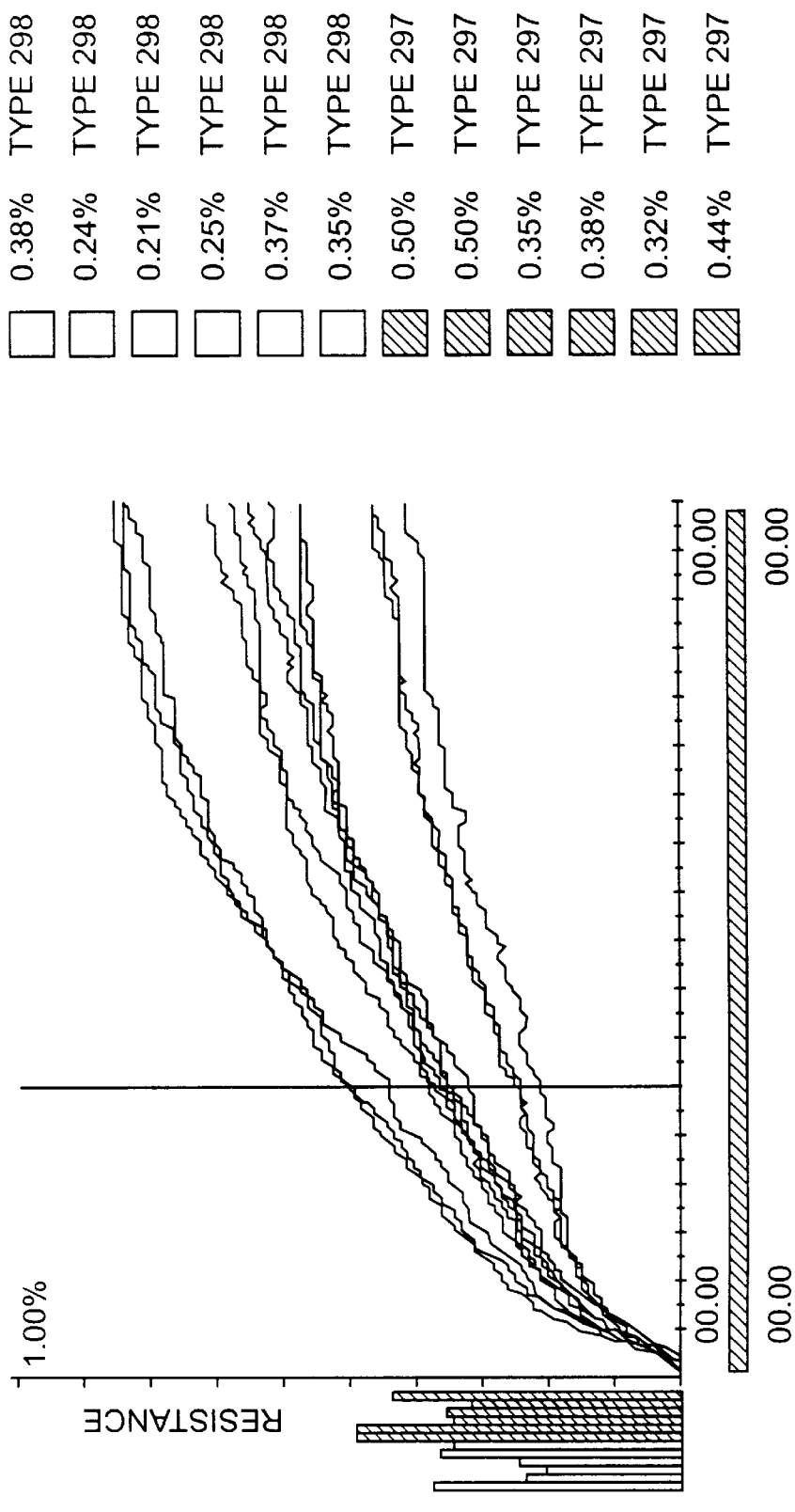
FIG. 3 is a graph showing the difference, for each sensor, between the signal of the sensor when exposed to (R)-(−)-2-amino-1-butanol as compared to the signal of the sensor when exposed to the (S) isomer, i.e. it is a plot of the difference between the graphs of FIGS. 1 and 2.

The difference between the signal of each sensor when exposed to the (R)-(−) enantiomer and the signal when exposed to the (S)-(+) enantiomer is shown in FIG. 3 which clearly shows that all the sensors are able to discriminate between the two enantiomers.

Example 4

A procedure similar to that described in Example 3 is repeated except that the sensors are exposed in turn to the two enantiomers of limonene. The resulting difference plot is shown in FIG. 4.

Figure 4:
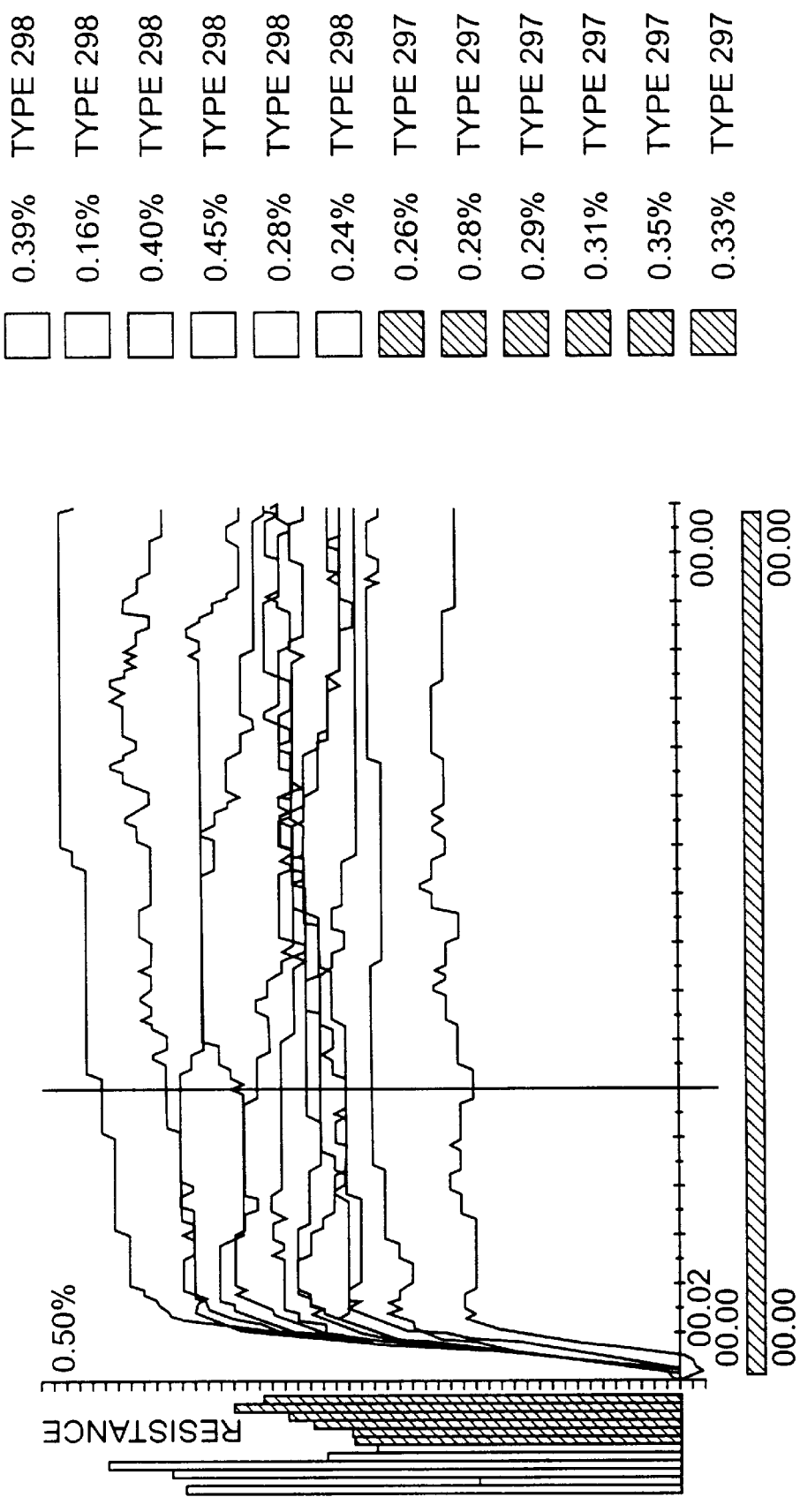
FIG. 4 shows a plot of the difference in the signals of twelve sensors when exposed to (R)-(+)-limonene and (S)-(−)-limonene.

It is clear from FIG. 4 that the sensors are able to discriminate between the two enantiomers of limonene.

Example 5

The procedure of Example 1 was followed except that a racemic mixture of sodium camphor sulphonate was used instead of resolved (R)(−) camphor sulphonic acid.

Example 6

Figure 5:
FIG. 5 shows a polar plot of the signal from ten sensors exposed to (S)-(+)-carvone.
Figure 5:
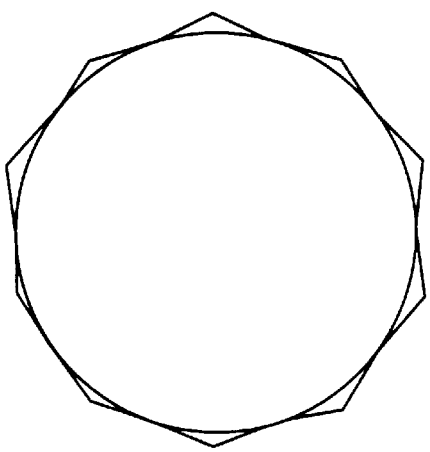

Ten sensors made by the procedure set out in Example 5 were exposed to the (S)-(+)-carvone and the resulting steady-state signals from the sensors are shown in the polar plot of FIG. 5.

Figure 6:
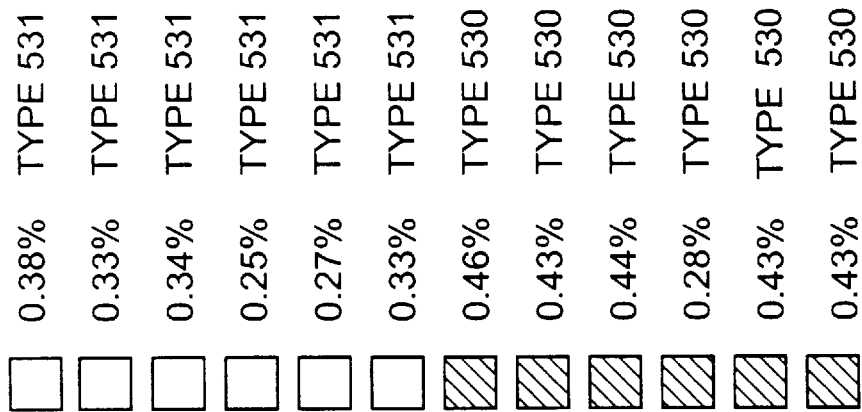
FIG. 6 is a polar plot similar to FIG. 5 but showing the response of twelve sensors of same type used in connection with the plot of FIG. 5 when exposed to (R)-(−)-carvone.
Figure 6:
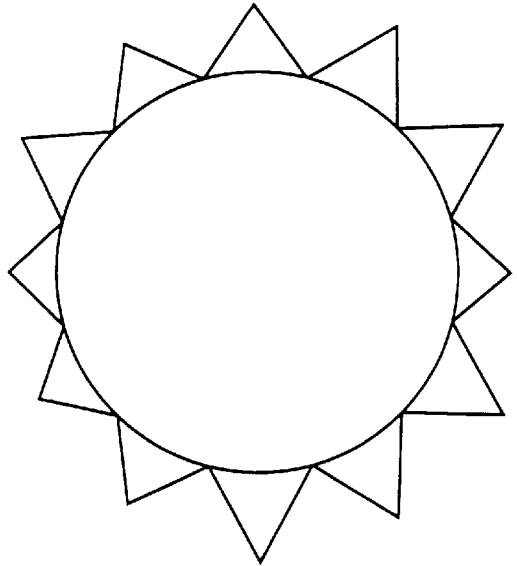

Twelve sensors of the same type were then exposed to (R)-(−)-carvone and the resulting polar plot (on the same scale as in FIG. 5) is shown in FIG. 6.

It is clear from a comparison between FIGS. 5 and 6 that the sensors are able to discriminate between the two enantiomers of carvone. Note should be taken that a polymer containing a racemic mixture of the counterion was still able to discriminate between the two enantiomers of carvone indicating that it is not necessary for all the sites in the polymer to have the same chirality in order to discriminate between different enantiomers.

We claim:

1. A sensor for distinguishing between different volatile enantiomeric compounds in a gaseous sample, the sensor comprising: a pair of contacts that are spaced by a gap; and a semi-conductive polymer material spanning the gap between the contacts; wherein the polymer material has an electrical resistance that changes upon exposure to said different volatile enantiomeric compounds in said gaseous sample substance and wherein the polymer material includes chiral sites.

2. The sensor of claim 1, wherein the chiral sites in the polymer material are formed by incorporating a chiral counterion into the polymer material.

3. The sensor of claim 2, wherein the chiral counterion is incorporated into the polymer material by growing the polymer material in the presence of the counterion.

4. The sensor of claim 2, wherein the chiral counterion is an optically active anionic counterion having an optically active site and includes a sulphonic acid (sulphonate) group.

5. The sensor of claim 4, wherein the sulphonic acid group is bonded directly to the optically active site.

6. The sensor of claim 2, wherein the chiral counterion is a compound of a general formula:

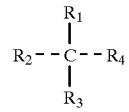

wherein $R_1$, $R_2$, $R_3$, and $R_4$ are all different substituents.

7. The sensor of claim 6, wherein at least one of the substituents $R_1$, $R_2$, $R_3$, and $R_4$ contains one or more sulphonate group(s).

8. The sensor of claim 2, wherein the counterion is selected from the group consisting of camphor sulphonate, amino acid anions, menthoxy acetate and carzyl acetate.

9. The sensor of claim 1, wherein the polymer material has a backbone polymer chain and the chiral sites in the polymer material are formed by chiral side groups bonded to the backbone polymer chain.

10. The sensor of claim 9, wherein the chiral side groups are selected from the group consisting of radicals formed from menthoxy acetic acid, carzyl acetate and chiral amino acids.

11. The sensor of claim 10, wherein the chiral amino acids are selected from the group consisting of cysteine and valine.

12. The sensor of claim 1, wherein the chiral sites in the polymer material are formed by growing the polymer from a monomer solution having an optically active solvent.

13. A method of detecting and distinguishing between different volatile enantiomeric compounds in a gaseous sample comprising:
 a) exposing the sensor as claimed in claim 1 to the gaseous sample containing said different volatile enantiomeric compounds;
 b) detecting resistance signals of the polymer material upon exposure of the polymer material to said different volatile enantiomeric compounds of said gaseous sample;
 c) analyzing a difference in said resistance signals of said polymer material; and
 d) distinguishing between said different volatile enantiomeric compounds in said gaseous sample based on the difference in said resistance signals of said polymer material.

* * * * *